(12) United States Patent
Molzahn et al.

(10) Patent No.: US 8,324,434 B2
(45) Date of Patent: Dec. 4, 2012

(54) HYDROGENATION PROCESS

(75) Inventors: David C. Molzahn, Midland, MI (US);
Kenneth A. Burdett, Midland, MI (US);
William L. Gibson, Humble, TX (US);
Karel J. Kriel, Houston, TX (US);
James E. McCreight, Cleveland, TX (US); Indresh Mathur, Sugar Land, TX (US)

(73) Assignee: Dow Global Technologies, LLC, Midland, MI (US)

( * ) Notice: Subject to any disclaimer, the term of this patent is extended or adjusted under 35 U.S.C. 154(b) by 31 days.

(21) Appl. No.: 12/918,814

(22) PCT Filed: Feb. 28, 2009

(86) PCT No.: PCT/US2009/035605
§ 371 (c)(1),
(2), (4) Date: Nov. 29, 2010

(87) PCT Pub. No.: WO2009/111352
PCT Pub. Date: Sep. 11, 2009

(65) Prior Publication Data
US 2011/0060168 A1    Mar. 10, 2011

Related U.S. Application Data

(60) Provisional application No. 61/032,994, filed on Mar. 2, 2008.

(51) Int. Cl.
*C07C 27/00* (2006.01)
(52) U.S. Cl. ..................................... 568/861
(58) Field of Classification Search .................. None
See application file for complete search history.

(56) References Cited

U.S. PATENT DOCUMENTS

| | | | |
|---|---|---|---|
| 2,036,940 A | 4/1936 | Holmes | |
| 3,920,716 A | 11/1975 | Spitz et al. | |
| 4,590,320 A | 5/1986 | Sapre | |
| 4,642,394 A | 2/1987 | Che | |
| 4,929,798 A | 5/1990 | de Lasa | |
| 5,107,018 A | 4/1992 | Schuster | |
| 5,164,309 A | 11/1992 | Gottschalk | |
| 5,210,335 A | 5/1993 | Schuster et al. | |
| 5,214,219 A | 5/1993 | Casale et al. | |
| 5,254,467 A | 10/1993 | Kretschmann | |
| 5,276,181 A | 1/1994 | Casale et al. | |
| 5,306,847 A | 4/1994 | Gehrer et al. | |
| 5,326,912 A | 7/1994 | Gubitosa et al. | |
| 5,354,914 A | 10/1994 | Gubitosa et al. | |
| 5,395,990 A * | 3/1995 | Scarlett | 568/864 |
| 5,426,249 A | 6/1995 | Haas et al. | |
| 5,496,786 A | 3/1996 | Gubitosa et al. | |
| 5,543,379 A | 8/1996 | Gubitosa et al. | |
| 5,599,689 A | 2/1997 | Haynie et al. | |
| 5,616,817 A | 4/1997 | Schuster et al. | |
| 5,686,276 A | 11/1997 | Laffend et al. | |
| 5,814,112 A | 9/1998 | Elliott et al. | |
| 6,080,898 A | 6/2000 | Drent et al. | |
| 6,207,865 B1 | 3/2001 | Breitscheidel et al. | |
| 6,288,287 B2 | 9/2001 | Ueoka et al. | |
| 6,479,713 B1 | 11/2002 | Werpy et al. | |
| 6,603,048 B1 | 8/2003 | Corbin et al. | |
| 6,677,385 B2 | 1/2004 | Werpy et al. | |
| 6,841,085 B2 | 1/2005 | Werpy et al. | |
| 6,900,361 B2 | 5/2005 | Elliott | |
| 7,038,094 B2 | 5/2006 | Werpy et al. | |
| 7,056,439 B2 | 6/2006 | Baniel et al. | |
| 7,135,309 B1 | 11/2006 | Laffend et al. | |
| 7,355,083 B2 | 4/2008 | Tuck et al. | |
| 7,371,558 B2 | 5/2008 | Cervin et al. | |
| 7,488,855 B2 | 2/2009 | Park et al. | |
| 7,582,457 B2 | 9/2009 | Dunn-Coleman et al. | |
| 7,968,704 B2 | 6/2011 | Hirth et al. | |
| 2002/0132311 A1 | 9/2002 | Seyfried et al. | |
| 2003/0153795 A1 * | 8/2003 | Crabtree et al. | 568/861 |
| 2005/0014238 A1 | 1/2005 | Seyfried et al. | |
| 2005/0244312 A1 | 11/2005 | Suppes et al. | |
| 2007/0123739 A1 | 5/2007 | Crabtree et al. | |
| 2008/0131945 A1 | 6/2008 | Toraya et al. | |
| 2008/0315151 A1 | 12/2008 | Suppes et al. | |
| 2010/0019192 A1 | 1/2010 | Suppes et al. | |

FOREIGN PATENT DOCUMENTS

| | | |
|---|---|---|
| CN | 1357628 A | 7/2002 |
| CN | 1434122 A | 8/2003 |
| CN | 1570123 A | 1/2005 |
| CN | 1635122 A | 7/2005 |
| CN | 1648207 A | 8/2005 |
| DE | 4128692 | 3/1993 |
| DE | 4238492 | 5/1994 |
| DE | 4302464 | 8/1994 |
| EP | 0510238 | 10/1992 |
| EP | 0523014 | 1/1993 |
| EP | 0523015 | 1/1993 |

(Continued)

OTHER PUBLICATIONS

Montassier et al., "Conversion of polyols by liquid phase heterogeneous catalysis over metals", Bulletin de la Societe Chimique de France, 1989, No. 2, p. 148-155.
Dasari et al., "Low-pressure hydrogenolysis of glycerol to propylene glycol", Applied Catalysis A, 2005, 281, p. 225-231.
PCT/US2009/035605 International Search Report and Written Opinion, mailed Feb. 28, 2009.

(Continued)

*Primary Examiner* — Sudhakar Katakam
(74) *Attorney, Agent, or Firm* — Lois K. Ruszala; KSJLaw, LLC

(57) ABSTRACT

The present invention provides an improved hydrogenation processes wherein heat is efficiently managed so that catalyst productivity is optimized. More particularly, in the processes of the present invention, a nonaqueous solvent is added to a reactant to provide a nonaqueous solvent/reactant mixture that can act as a heat sink and absorb at least a portion of the heat generated within the reactor. Desirably, a reaction product, or a solvent with a minimal number of hydroxyl groups, is utilized so that the formation of unwanted byproducts can be minimized.

10 Claims, 7 Drawing Sheets

FOREIGN PATENT DOCUMENTS

| | | |
|---|---|---|
| EP | 0598228 | 5/1994 |
| EP | 1000003 | 10/2002 |
| EP | 1369488 A1 | 10/2003 |
| EP | 1889825 | 2/2008 |
| FR | 2862644 A1 | 5/2005 |
| JP | 8294394 A | 11/1996 |
| WO | 9905085 | 2/1999 |
| WO | 2005021476 A1 | 3/2005 |
| WO | 2005051874 | 6/2005 |
| WO | 2005095536 | 10/2005 |
| WO | 2007053705 | 5/2007 |

* cited by examiner 15 g Raney copper Continuous Reactor Run

HYDROGENATION PROCESS

Cross Reference to Related Applications

This is a 371 application of PCT International Patent Application Number PCT/US2009/035605, filed Feb. 28, 2009, which claims priority to U.S. provisional patent application Ser. No. 61/032,994, filed Mar. 2, 2008. Each of these applications is incorporated herein by reference in their entirety for any and all purposes.

FIELD OF THE INVENTION

The present invention provides an improved hydrogenation process. More particularly, in the hydrogenation process of the present invention, a nonaqueous solvent is utilized to manage heat within the reactor. By thus minimizing water added to the process, catalyst activity and reaction specificity are enhanced. Desirably, a reaction product, or a solvent with a minimal number of hydroxyl groups, is utilized so that the formation of byproducts can be further minimized or avoided.

BACKGROUND

Hydrogenation reactions are typically highly exothermic, and as such, care must be taken in order to control reaction temperatures so that proper reaction conditions are maintained and desired reaction products are obtained. On a commercial scale, this may typically be done by utilizing a reactor that facilitates heat removal. Tubular reactors, fluidized bed reactors and jacketed, stirred tanks are all examples of reactors whose design allows for the circulation of coolant, typically in a jacket external to the reactor. While effective at heat management, each of these requires the expenditure of additional resources in order to maintain isothermal conditions within the reactor.

Solvents may also be utilized to manage heat generated by exothermic hydrogenation reactions, and in particular, water has been utilized for this purpose. However, the addition of water into such reactions can be undesirable in that it typically must be removed to provide commercially acceptable end products, adding cost and time to the process. Additionally, extraneous water can decrease the activity of any catalyst desirably used in the process, in some cases, can even contribute to catalyst degradation, and may actually slow reaction times.

One commercially important example of a hydrogenation reaction involves the conversion of glycerin to provide a distribution of glycols including, e.g., 1,2-propanediol, 1,3-propanediol, 1,2-ethanediol, etc. In the conventional process, glycerin and hydrogen or a hydrogen-containing gas are heated to a reaction temperature in the presence of a catalyst, most typically a copper containing catalyst. Such conventional processes, unfortunately, can provide suboptimal productivity.

Firstly, low activity and poor catalyst lifetime can limit the productivity of conventional catalysts for this particular hydrogenation reaction. Also, and although, e.g., 1,2-propanediol may be the desired end product, the formation of other glycols, such as 1,3-propanediol, 1,2-ethanediol and other by-products can increase under certain reaction conditions, such as a wide variation in temperature, the presence of excess water, the low selectivity of some conventional copper containing catalysts or the use of lower grade reactants, etc. Reaction selectivity may be influenced to favor production of a particular product, or disfavor production of reaction by-products, by adjustment of one or more reaction conditions, although such adjustment typically does not come without expense. And, less desirable glycols and/or typical reaction by-products, e.g., hexanediol and propylene glycol propionates, can be difficult, if not impossible, to remove by distillation techniques.

Desirably then, an improved hydrogenation process would be provided in which heat could be adequately managed without the addition of substantial amounts of water. Effective heat management should prevent substantial degradation in catalyst activity or selectivity. Further advantage could be seen if the process were economically practical, or even advantageous, by the productive utilization of the energy of reaction generated thereby. Applicability of the process to a variety of grades of starting materials would further enhance the commercial significance thereof, as would utilization of catalysts having a longer lifetime and capable of exhibiting a higher activity and/or selectivity for the desired reaction products than catalysts conventionally utilized in this process.

BRIEF SUMMARY OF THE INVENTION

The present invention provides an improved hydrogenation process that meets or exceeds these expectations. The inventive process provides effective heat management without the addition of substantial amounts of water. Because heat is effectively managed, adiabatic reactors may be utilized and/or the process may proceed substantially continuously. Catalyst productivity is also optimized, so that reaction rate and selectivity are not compromised. Because the formation of byproducts is minimized, and the use of substantial amounts of water is avoided, the present process is simplified. Further cost savings can be provided via the productive utilization of the heat of reaction generated by the hydrogenation process to further reduce any water generated by the process.

More specifically, and in a first embodiment then, the present invention provides an improved hydrogenation process. The process provides for the addition of a nonaqueous solvent to a hydrogenation reaction, either individually or in combination with a reactant thereof. The nonaqueous solvent desirably has hydroxyl functionality therein limited, and more specifically, the nonaqueous solvent desirably comprises a hydroxyl group weight percent of less than about 45%, preferably less than about 30%, and more preferably less than about 15% and a hydroxyl equivalent weight of greater than about 30, preferably greater than about 40 and more preferably, greater than about 100. Preferred nonaqueous solvents include, but are not limited to, dioxane, propylene glycol, propylene glycol methyl ether, polyethylene glycols, polyethylene glycol methyl ethers, tripropylene glycol, tripropylene glycol methyl ether, dipropylene glycol, dipropylene glycol methyl ether, phenoxyethanol, diphenyloxide or combinations of these.

In certain preferred embodiments, the nonaqueous solvent may comprise a recycled reaction product stream which may comprise reaction product, a reactant, reactant byproducts or combinations thereof. Desirably, the recycled reaction product stream will comprise less than about 17% water, and may have the water content thereof further reduced prior to its combination with the reactant and/or introduction into the hydrogenation reaction. The improved hydrogenation process provides reactant conversion of at least about 65%, preferably at least about 75% and in some instances, at least about 85% reactant conversion, while also providing final product selectivity of at least about 75%, or up to 80%, or even 85%. Additionally, the use of a reaction product may allow application of inexpensive purification techniques to the reaction product/reactant mix, which in turn may advantageously allow a lower grade of reactant to be used in the inventive hydrogenation process.

In a further embodiment, the invention provides an improved process for the hydrogenation of glycerol. The process comprises (a) combining a glycerin feedstock with a nonaqueous solvent to provide a dewatered feedstock having less than about 5 weight percent water and then (b) contacting the dewatered feedstock with hydrogen in the presence of a catalyst at operating feedrates, temperature and pressure conditions sufficient to result in the formation a reaction product comprising less than about 17% water, or less than 10% water, or even less than about 6% water. In certain embodiments, at least a portion of the reaction product is recycled and combined with, or utilized as, the nonaqueous solvent. In these embodiments, the reaction product/reactant mix may assist in temperature control within the reactor so that the operating temperature does not vary by more than about 100° C., and preferably does not vary by more than about 50° C. Furthermore, the reaction product/reactant mix may be more amenable to inexpensive purification techniques than the reactant alone, so that lower grades of reactants may be utilized and further cost savings provided to the inventive hydrogenation process.

DESCRIPTION OF THE DRAWINGS

The detailed description of the invention that follows may be further understood and/or illustrated when considered along with the attached drawings. In order to simplify the drawings, conventional details, such as valves, pumps condensers, reboilers, surge tanks, flow and temperature control devices and others like these may have been omitted in certain instances. The construction, operation and function of such devices, as well as the appropriate use thereof in process design, is believed to be known to those of ordinary skill in the chemical engineering art and as such, the omission or inclusion of these conventional elements is not meant to belie any particular importance thereto.

DETAILED DESCRIPTION OF THE INVENTION

Figure 1:
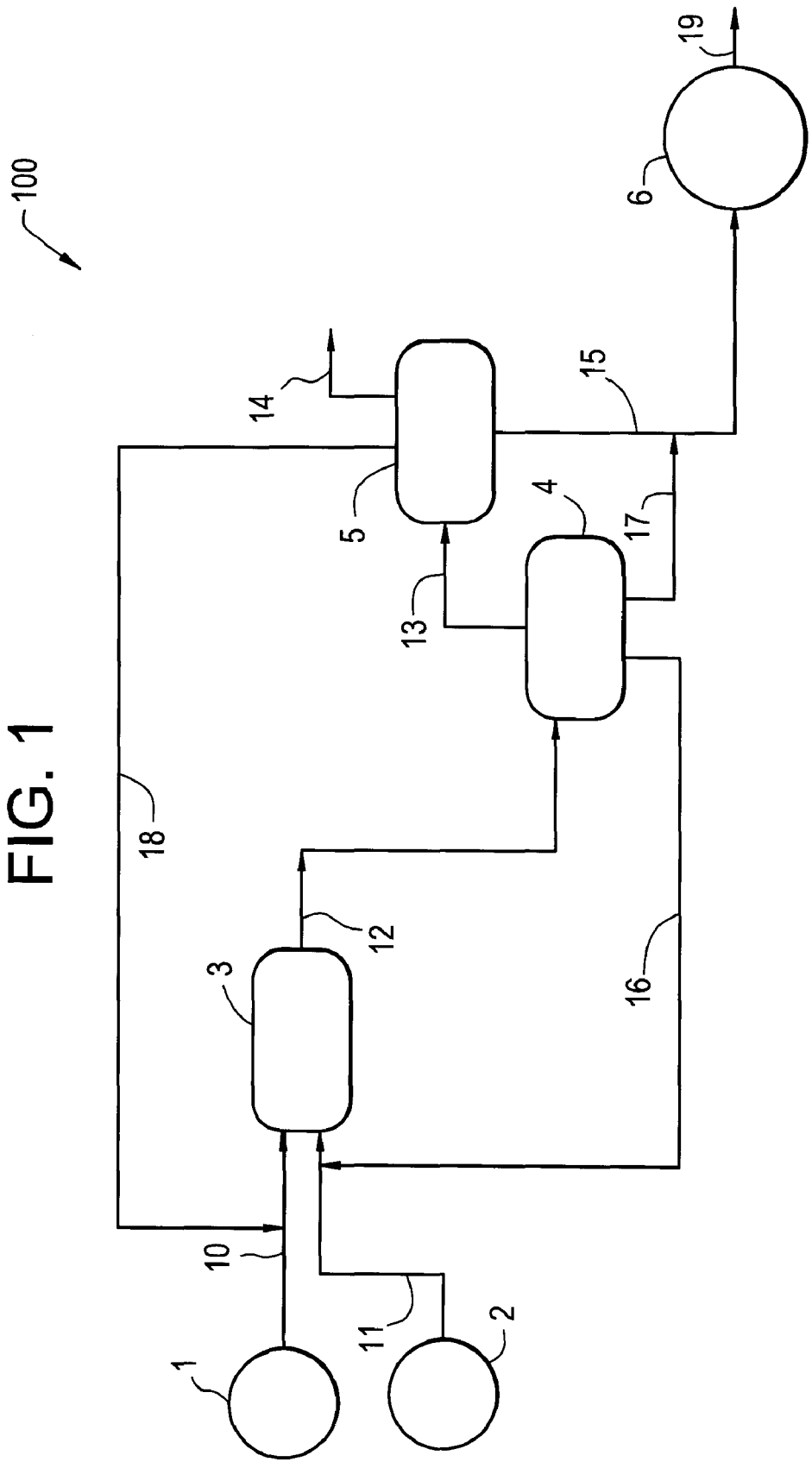
FIG. 1 is a block diagram of an apparatus that may be utilized to carry out a hydrogenation process according to the present invention.

The present invention provides an improved hydrogenation process. More particularly, the improved process utilizes a nonaqueous solvent for heat management, and since the introduction of water is minimized, catalyst productivity is optimized and product selectivity is desirably enhanced. The nonaqueous solvent is desirably one in which hydroxyl groups are limited and in which the reactants are sufficiently soluble so that reactant conversion may advantageously be maintained or even enhanced. Cost savings can thus be provided in equipment expenditure in that a greater variety of reactors are amenable for use in the process, including those that are easier to use and less expensive to operate than jacketed or otherwise cooled reactors.

The nonaqueous solvent may be further characterized as one in which the number of hydroxyl groups is limited, i.e., one with a percent hydroxyl weight of less than about 45%, preferably less than about 30% and more preferably less than about 15%, and with a hydroxyl equivalent weight of greater than about 30, preferably greater than about 40, and more preferably, greater than about 100. In certain preferred embodiments, the nonaqueous solvent may be a reaction product, reactant or combinations of these so that the formation of undesirable byproducts, as may be facilitated by the addition of other types of solvents, can be minimized or even eliminated. Further advantages can be seen if the nonaqueous solvent has the amount of water therein kept to a minimum, i.e., desirably below about 5 weight percent.

In those embodiments of the invention wherein a reaction product/reactant mix is utilized, the inventive process may provide further advantages in that lower grades of reactant may be utilized than in conventional processes. That is, the reaction product/reactant mix can be more amenable to inexpensive purification techniques than the reactant alone, so that once combined, the reaction product/reactant mix can be subjected to said purification techniques. The relatively pure reactant that results is introduced into the process, and avoids the expense of purchasing a refined grade of reactant, as well as the application of more expensive techniques.

The present process may advantageously be applied to any hydrogenation process and any hydrogenation process so improved may be carried out substantially continuously, i.e., so that reactant feedstocks are provided to the reactor substantially continuously and reaction products are removed from the reactor at a rate sufficient to minimize or prevent the accumulation of reaction product within the reactor. Reactors that are suitable for continuous reactions are known in the art and include fixed bed reactors, fluidized bed reactors, continuous stirred tank reactors and reactive distillation columns. Since the process of the present invention provides a self reliant means of heat management, an adiabatic reactor, i.e., one not heated or cooled from an external source, may be utilized.

Hydrogenation reactions desirably utilizing a catalyst find particular benefit, in that catalyst activity is optimized when variations in reaction conditions are minimized, and the addition of solvents extraneous to the reaction is avoided. In particular, reactions desirably utilizing catalysts whose activity and/or selectivity are detrimentally impacted via the addition of aqueous solvents are benefited since nonaqueous solvents are desirably utilized in the present process.

One particularly important application of the process of the present invention is found in the hydrogenation of glycerol. Although in the conventional process of conducting this hydrogenation reaction, selectivity can suffer from less than optimal heat management and/or the addition of excess water, the present process is not so compromised. Rather, the process of the present invention avoids the introduction of excess water and yet manages heat effectively via the introduction of a nonaqueous solvent. Also, the heat of reaction generated may actually be used to remove at least a portion of any water generated. As such, temperature variation within the reactor is minimized and catalyst activity and selectivity are at least maintained, and desirably improved.

In the hydrogenation process according to the present invention, glycerin is combined with a nonaqueous solvent and hydrogen in the presence of a catalyst and at feedrates, operating temperature and pressure conditions sufficient to result in the formation of a reaction product with a minimal water content. Although the amount of water generated by the process will vary depending upon at least the reactant feed rates, and temperature and pressure within the reactor, as one example, at a glycerin feed concentration of 30% and assuming 100% conversion, the resulting reaction product is expected to comprise less than, e.g., about 17% water, less than about 10% water or even less than about 6 weight percent water.

Reaction products having such a low water content provide significant advantages at least in a reduction in any need for further processing to remove water. In certain embodiments, however, water content of the reaction products may be even further reduced by utilizing at least a portion of the heat of reaction generated by the hydrogenation reaction to vaporize or otherwise remove at least a portion of any water from the reaction products. Desirably, an amount of water will be removed so that 15% or less remains in the reaction products, more desirably, 10% or less, and optimally, the reaction products will comprise less than about 5% water. The removal of water is expected to assist in heat management within the reactor, as well as to help maintain the catalyst activity and selectivity.

The inventive hydrogenation process provides glycerin conversions of at least about 50%, or at least about 65%, or at least about 75%, and even about 85%. Reaction selectivities are likewise optimized, although the particular reaction product provided can be influenced by the reaction conditions. Generally speaking, for those embodiments of the invention wherein the hydrogenation process is desirably used to convert glycerin to propylene glycol, appropriate reaction conditions may include operating temperatures of from about 150° C. to about 250° C., or from about 160° C. to about 220° C. and operating pressures of from about 1 MPa to about 5 MPa or even from about 1.5 MPa to about 3 MPa. For this conversion, and under these operating conditions, the present inventive process can provide propylene glycol selectivities of at least about 75, or even 85, or up to about 95.

The nonaqueous solvent may be combined with the glycerin prior to, along with, or after the hydrogen is introduced to the reactor. In those embodiments wherein the nonaqueous solvent comprises a reaction product, it is preferably combined with the glycerin prior to the introduction of hydrogen, and even more preferably, the nonaqueous solvent comprising a reaction product is combined with the glycerin feedstock prior to its introduction into the reactor. In such embodiments, the nonaqueous solvent/reaction product may act as a diluent to the hydrogenation reaction, absorbing excess heat, and assisting in minimization of temperature variation within the reactor, i.e., so that the temperature therein does not vary by more than about 100° C., and preferably does not vary by more than 50° C., of the operating temperature.

Desirably, the recycled reaction product will have a temperature of from about 140° C. to about 200° C., and its utilization as the nonaqueous solvent and mixing with the glycerin feedstock will thus raise the temperature of the glycerin sufficiently so that the temperature within the reactor will be within this range. If necessary or desired, external heat may be applied to the recycled reaction product, the recycled reaction product/glycerin combination or the reactor in order to maintain an effective operative temperature for the hydrogenation process.

In those embodiments of the invention wherein the nonaqueous solvent comprises a reaction product, one or more additional nonaqueous solvents may be utilized as well. In these embodiments, the multiple nonaqueous solvents may be utilized separately, or in any combination configuration, i.e., two nonaqueous solvents may be combined and utilized together, while another is introduced separated, etc. As but one particular example, when the nonaqueous solvent comprises a reaction product, the reaction product may be combined with a reactant, and may or may not be subjected to one or more purification techniques prior to introduction into the reactor, and one or more additional nonaqueous solvent may be added directly to the reactor, prior to, along with, or subsequent to the introduction of the reaction product/reactant mix.

Embodiments of the invention wherein the nonaqueous solvent comprises a reaction product are particularly advantageous in that the reaction product/reactant mix may be subjected to purification techniques that may be less effective when applied to the reactant alone but are relatively inexpensive as compared to those conventionally used to purify or refine the same reactants. For example, in those embodiments of the invention wherein the hydrogenation process is one for the hydrogenation of glycerin to form propylene glycol, the glycerin may be combined with a portion of the propylene glycol produced and then subjected to purification/refinement techniques that are less effective, or completely ineffective, when applied to glycerin alone. As such, crude glycerin may be employed, providing a substantial cost savings over the use of refined glycerin as a starting material.

Additionally, the purification/refinement techniques employed in this embodiment of the invention may also be less costly than conventional techniques for the purification of crude glycerin, providing further cost savings. More particularly, whereas pure crude glycerin is not particularly amenable to distillation, typically requiring the use of wiped film or thin film evaporators in order to be purified, crude glycerin mixed with propylene glycol can be distilled to remove lightweight contaminants therefrom. Distillation columns can be less costly both to purchase and to operate than either wiped or thin film evaporators.

In any case, and whatever the nonaqueous solvent utilized, some unreacted amount of the nonaqueous solvent may be present in the reaction product stream produced by the process and if so, may desirably be removed. Any nonaqueous solvent removal technique can be utilized for this purpose, the suitability of which will depend on the boiling point of the nonaqueous solvent relative to the reaction product stream. Those of ordinary skill in the chemical engineering art are well versed in such techniques and capable of selecting and implementing one appropriate based upon the nonaqueous solvent utilized if removal of the same is desired or required.

Several catalysts are known that are suitable for hydrogenation processes. These include catalysts at least minimally useful for facilitating the breaking of carbon-oxygen or carbon-carbon bonds required in the processes, such as those including elements of the subgroups from Group I, Group VI, and/or Group VIII on the periodic table. More particularly, suitable catalysts for hydrogenation processes include those comprising metals such as chromium, cobalt, copper, nickel, palladium, platinum, rhodium, ruthenium, tungsten, zinc and combinations thereof.

Suitable catalysts can differ in their reaction temperature requirements as well as the selectivity for particular hydrogenation products, and can be chosen accordingly. Additionally, catalysts exhibiting an open structure, with a minimum micropore volume, and a relatively large surface area as compared to conventional catalysts, may be particularly useful to at least partially avoid mass transfer limitations that may otherwise plague catalysts used in hydrogenation reactions. In those preferred embodiments of the present invention wherein glycerin is desirably hydrogenated to provide, e.g., propylene glycol, a copper-containing catalyst can be advantageously utilized, and of these copper chromium catalysts provide good selectivity toward propylene glycol in such processes.

Exemplary suitable catalysts include those containing copper as an active component, such as those prepared from copper zinc alloys, copper-zinc oxides (Cu/ZnO), copper-aluminum oxides (Cu/Al$_2$O$_3$), copper zirconium oxide, (Cu/ZrO$_2$), copper on carbon (Cu/C) and copper silicon dioxide (Cu/SiO$_2$). Other transition metals, including barium, manganese, zirconium, cerium, and the like, in the form of their oxides may be combined with such copper-based catalysts in small amounts if doing so is expected to provide improved catalyst properties. Suitable catalysts may also include reaction promoter co-metals, e.g., chromium, cobalt and zinc, if the same is expected to be beneficial.

One preferred class of copper-containing catalysts is that comprising the copper chromite catalyst $(CuO)_x(Cr_2O_3)_y$, generally commercially available. The nominal compositions of copper expressed as CuO and chromium expressed as Cr$_2$O$_3$ may vary from about 60-99 wt % of CuO and 1-40 weight percent of Cr$_2$O$_3$. Preferred compositions are those containing about 85-99 copper and about 1-15 weight percent chromium. Typically, the surface area of these catalysts may be greater than about 50 m$^2$/g, greater than about 60 m$^2$/g, or even up to about 70 m$^2$g.

It has now been surprisingly discovered that the utilization of a low, and in certain embodiments, almost no micropore volume catalyst, may also advantageously be utilized in the present inventive process. More particularly, the use of copper aluminum catalysts, Cu/Al⁻50-55%/50-45% with low, or substantially no micropore volume, has also been found to provide the present process with glycerin conversions of at least about 50%, or even up to about 60%, and selectivities to propylene glycol of greater than about 80%, or even greater than about 90%, or even greater than about 95%. Preferred catalysts among these include those having a total surface area of at least about 10 m$^2$/g, or at least about 12 m$^2$g, or up to about 15 m$^2$/g or even greater. Many such catalysts are commercially available, and one example of these is commercially available from W. R. Grace under the tradename Raney®.

Turning now to FIG. 1, there is illustrated one configuration of an apparatus that can be utilized to carry out the present inventive hydrogenation process. Hydrogenation apparatus 100 includes hydrogen feedstock 1, reactant feedstock 2, reactor 3, separator 4, condenser 5, and product reservoir 6.

In use, hydrogen and feedstock are provided to reactor 3 from hydrogen feedstock 1 and reactant feedstock 2, respectively, where they come into contact in the presence of a catalyst to form reaction products that are discharged from reactor 3 to vapor liquid separator 4 through line 12. Although the exemplary conversion of glycerin to propylene glycol will be used in the discussion of FIG. 1, the inventive process is not so limited, and any hydrogenation process can be conducted by apparatus 100.

Hydrogen is provided from hydrogen feedstock 1 to reactor 3 via hydrogen line 10 at a pressure sufficient to provide dissolved hydrogen in the liquid phase to react with glycerol, or at a pressure from at least about 1.5 MPa to about 8 MPa. Hydrogen is desirably provided in a molar excess of that required for the hydrogenation reaction, or in amounts of from about 1.2 times to about 25 times the molar requirement for the hydrogenation reaction.

Glycerin is provided from reactant feedstock 2 to reactor 3 via reactant line 11, at a rate of from about 0.04 weight hourly space velocity(WHSV) to about 1.0 WHSV at a temperature of from about 140° C. to about 200° C., and at a pressure of from about 1.5 MPa to about 8 MPa. In the apparatus shown in FIG. 1, the glycerin provided from reactant feedstock 2 should desirably be somewhat purified, i.e., will desirably not contain more than about 0.1% of any substance that cannot be vaporized.

Reactor 3 can be any reactor suitable for carrying out a hydrogenation process, and advantageously, because the heat of the inventive process is sufficiently managed, can be an adiabatic reactor. Although the conditions within reactor 3 will vary depending on the type of reactor in use, and further can be purposefully varied to drive the hydrogenation toward formation of a particular reaction product, in that embodiment of the invention wherein the reactor is an adiabatic reactor, and glycerin is being preferentially converted to propylene glycol using a copper chromium catalyst, the temperature within reactor 3 can be from about 140° C. to about 250° C. The pressure in the reactor will desirably be sufficient to keep glycerin and most reaction product in the liquid phase but not so high that conversion rate and/or selectivity suffer, and is thus desirably from at least about 1.5 MPa to about 8 MPa.

Reactor 3 may include an amount of catalyst, provided in any format wherein contact between the reactants and the catalyst is facilitated to an extent so that the catalyst is able to at least marginally assist in the hydrogenation reaction, as by lowering the reaction temperature, increasing the reaction rate, etc. Typically, any catalyst is provided in packed or fluidized beds, and in those embodiments of the invention wherein reactor 3 comprises an adiabatic reactor, any catalyst may preferably be provided in fixed beds. Advantageously, the reintroduction of recycled reaction product liquid, combined with glycerol is expected to ameliorate any high temperatures that may otherwise occur with the fixed provision of catalysts within a reactor.

Vapor liquid separator 4 acts to separate the reaction product from reactor 3 into liquid and vapor portions, typically via a reduction in pressure on the reaction product stream. Vapor liquid separator 4 is desirably operated at conditions that will drive the desired amount of water and propylene glycol into the reaction product vapor and that minimize water in the reaction product liquid. Generally speaking then, the pressure within vapor liquid separator 4 may be from about 0.1 MPa to about 0.5 MPa or even from about 0.05 MPa to about 1.5 MPa. Desirably, vapor liquid separator 4 may be thermally coupled to with reactor 3 so that that the heat of reaction of the hydrogenation reaction can assist in driving the separation, although it may be necessary to add heat to or remove heat from the vapor liquid separator to obtain the desired separation and/or to ensure that the amount of evaporated product in stream 13 balances with the glycerin feedstock. Typically, the temperature within vapor liquid separator 4 will be from about 120° C. to about 200° C., or from about 140° C. to about 170° C.

The reaction product liquid may then be preferentially recycled to reactor 3 through stream 16 or optionally discharged from vapor liquid separator 4, via line 17 to product reservoir 6. In preferred embodiments of the invention, substantially all the liquid from the vapor-liquid separator 4 is recycled to the reactor 3 through line 16, and the flow through line 17 is low, and may even be zero. With this configuration it is possible to provide glycerin conversions of up to about 95%, even if the glycerol conversion over the reactor is low, e.g. from about 20% to about 30%. In either case, since glycerol is much less volatile than propylene glycol, the liquid from the vapor-liquid separator 4 (streams 16 and 17) contains almost all the glycerol not converted in the reactor 3, and may also comprise propylene glycol, water, and byproducts. More particularly, the reaction product liquid may likely comprise from about 60 weight percent to about 80 weight percent propylene glycol, from about 5 weight percent to about 35 weight percent glycerin, by products such as acetol, propanol and ethanediol in amounts of from about 1 weight percent to about 5 weight percent and no more than about 5 weight percent water.

Reaction product vapor is discharged from vapor liquid separator 4 through line 13 to condenser 5 where it is cooled to form a condensed reaction product that is discharged through line 15 to product reservoir 6. Any noncondensables, likely comprising mostly hydrogen and potentially including minor amounts of water vapor, are discharged through line 14 for disposal, or recycled via line 18 and combined with hydrogen in hydrogen line 10. The reaction product vapor is expected to contain primarily water, propylene glycol and hydrogen. More particularly, the reaction product vapor may likely comprise from about 0.5 weight percent to about 3 weight percent hydrogen, from about 15 weight percent to about 25 weight percent water, from about 60 weight percent to about 75 weight percent propylene glycol, and small amounts of volatile byproducts such as acetol and propanol.

Figure 2:
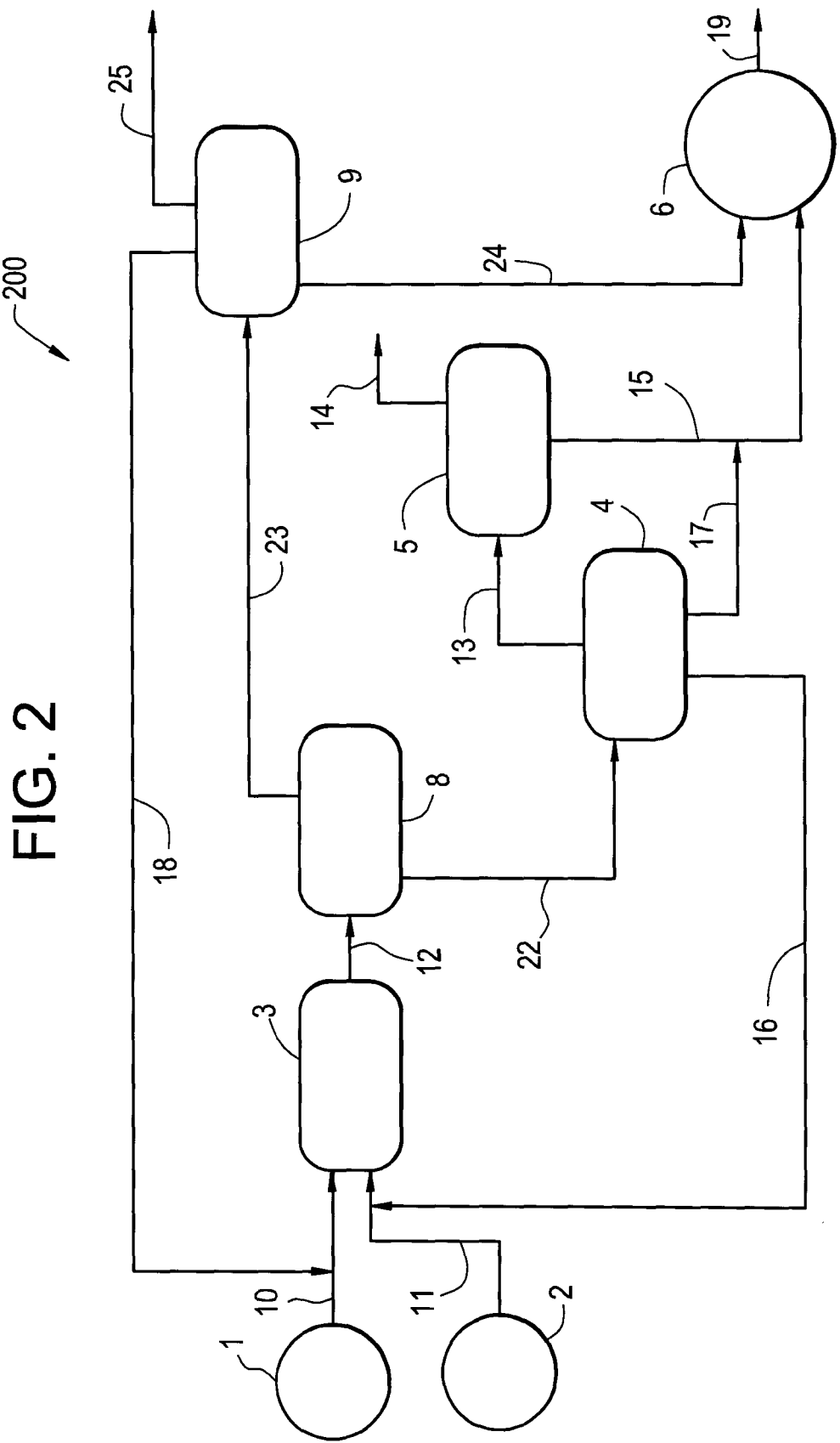
FIG. 2 is a block diagram of an additional apparatus that may be utilized to carry out a hydrogenation process according to the present invention.

Turning now to FIG. 2, there is illustrated an apparatus 200 that may also be used to carry out a process according to the present invention. Apparatus 200, in addition to the components of apparatus 100, includes an additional vapor liquid separator 8 and cooler 9. The components that apparatus 200 has in common with apparatus 100 are expected to perform in substantially the same manner and at substantially the same conditions, as discussed above in connection with FIG. 1, and will not be discussed further hereinbelow.

Vapor liquid separator 8 desirably acts to at least partially separate the effluent from reactor 3 into a vapor stream and a liquid stream, without changing the pressure substantially from the pressure within reactor 3. The reaction product vapor separated by vapor liquid separator 8 is discharged through line 23 to cooler 9 and is expected to contain propylene glycol, water, hydrogen, and byproducts. More particularly, the reaction product liquid may likely comprise at least about 40 weight percent propylene glycol, from about 1 weight percent to about 10 weight percent hydrogen, from about 50 weight percent to about 60 weight percent water, and the remainder made up of byproducts. The temperature within cooler 9 preferably is such that substantially all of the reaction product vapor is condensed, e.g., at a temperature of less than about 100° C. The liquid condensed in cooler 9 is transferred to the product reservoir 6 through line 24, while hydrogen freed of condensible liquids can be recycled to reactor 3 through line 18, or alternatively disposed of through line 24.

Vapor liquid separator 8 is fluidly coupled with vapor liquid separator 4 via line 22, and the reaction product liquid separated in vapor liquid separator 8 is transferred to vapor liquid separator 4 thereby. The vapor liquid separator 4 acts to separate the reaction product from reactor 3 into liquid and vapor portions, via a reduction in pressure on the reaction product stream, as described in connection with apparatus 100.

Figure 3:
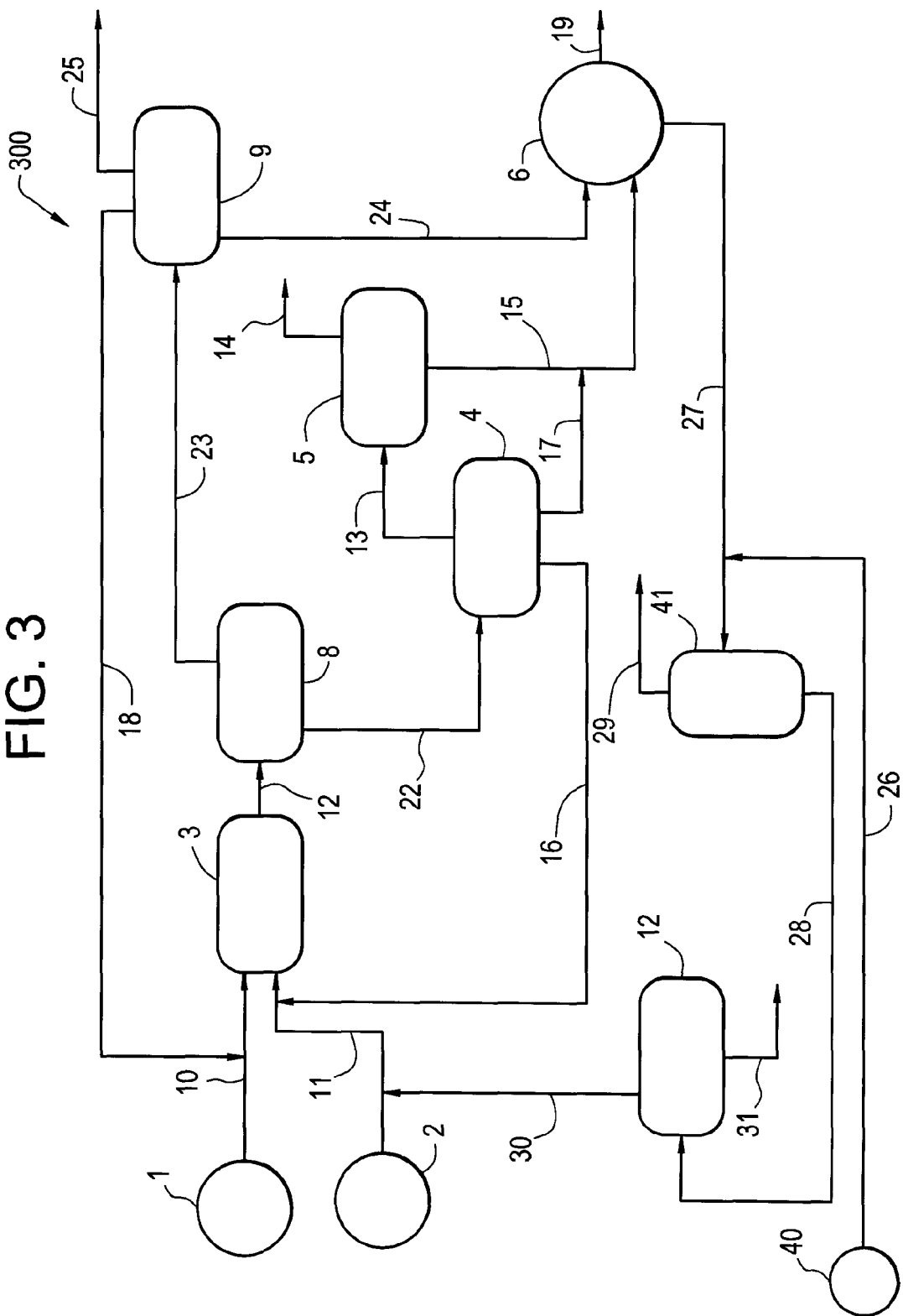
FIG. 3 is a block diagram of an additional apparatus that may be utilized to carry out a hydrogenation process according to the present invention, wherein the hydrogenation process utilizes crude glycerin.

Finally, FIG. 3 shows an apparatus 300 useful for performing the hydrogenation process of the present invention, and particularly, for performing that embodiment of the invention wherein crude glycerin is desirably utilized as a starting material, rather than refined or purified glycerin. In addition to those components disclosed and described in connection with FIGS. 1 and 2, apparatus 300 comprises crude reactant feedstock 40, line 27 and distillation column 41, so that crude reactant (in this instance of glycerin, containing typically 1-4% salts, in addition to methanol and water) can be used to supplement or replace reactant provided by reactant feedstock 2, which otherwise would desirably comprise less than 0.1% contaminants.

In operation of apparatus 300, a portion of the propylene glycol in product receiver 6 is withdrawn through line 27 and mixed with crude glycerin provided by crude reactant feedstock 40. The glycerin/propylene glycol mix, also containing water and other lights from both the crude glycerin and propylene glycol, is fractionated in distillation column 41. The water and other light components from both streams are withdrawn overhead, while the bottoms propylene glycol/glycerin mix is discharged through line 28 and is dry and free of water and lights. Advantageously, the relatively low boiling point of the propylene glycol (185°) makes it possible to remove the water and lights overhead without exposing the glycerin to excessively high temperatures.

The propylene glycol/glycerin mix discharged through line 28 is fed to the flash evaporator/condenser 12, where a vacuum as low as 10-30 mmHg can be obtained, due to the absence of water or other lights. The presence of propylene glycol additionally helps to evaporate the less volatile glycerin. The overhead vapor of the flash evaporator when condensed is substantially free of salts and other nonvolatiles and can be fed into reactor 3 to replace some or all of any purified glycerin provided by reactant feedstock 2. Salts and other nonvolatiles, as well as some portion of glycerin, may be discharged through line 31 and disposed of.

The reaction product composition present in product reservoir 6, in the case of either apparatus 100, 200 or 300, will desirably comprise propylene glycol (from about 70 weight percent to about 80 weight percent) and water (from about 18% to about 23%), and may also comprise trace amounts of unreacted glycerol, 1,2-ethanediol, alcohols such as ethanol and propanol, and acetol, and other reaction byproducts or intermediates. A reaction product provided by the process of the present invention is suitable for direct use as an end product in many applications, however, and if desired, the reaction product may be removed through line 19 and further processed to make additional end products.

COMPARATIVE EXAMPLE 1

This reaction was done to illustrate the addition of a minor amount, e.g., 5 weight percent water, on the conversion rate and selectivity of a conventional hydrogenation reaction wherein glycerin is desirably converted to propylene glycol.

400 g of a copper catalyst, BASF Cu-1234, 10-14 mesh was loaded into an oil jacketed reactor (2.54 cm od×83 cm long). The catalyst was activated by purging the reactor with nitrogen, and while purging, heating the reactor to a temperature of about 130° C. At this temperature, hydrogen (about 5% v/v) was added to the nitrogen purge and the reactor temperature raised to about 185° C. After 20 hours at 185° C., the hydrogen content in the nitrogen purge stream was increased to about 10% v/v. Thereafter the reactor temperature was maintained at about 185-190° C. for another 24 hours, and then cooled to 150° C.

A liquid feed composition of 60% glycerin (USP Grade) and 40% propylene glycol (crude grade, 95%) was initiated to the reactor at a rate set point of 1.0 ml/min, upflow, in concert with a 100% hydrogen gas flow at a rate of about 315 sccm. After three hours, the reactor temperature was raised to about 195° C. the pressure adjusted to about 2.75 MPa, and the liquid feed rate lowered to a rate set point of about 0.5 ml/min.

After 745 hours of operation, analysis of the resultant product stream showed an average glycerin conversion of 80% and average molar selectivity to propylene glycol of about 89% over a 100 hour period. After 100 hours, under these operating conditions, the liquid feed composition was adjusted to be about 37.5% glycerol, 57.5% propylene glycol and 5% water. Analysis of the resultant product stream showed an average glycerin conversion of 67% and an average molar selectivity to propylene glycol of 89% over a 70 hour period. The complete results for this example are shown in Table 1, below.

34 g of a copper chromium catalyst, Johnson-Matthey 60/35T, was loaded into a fixed bed oil jacketed reactor. The catalyst was activated at 185-200° C. with 5% hydrogen in nitrogen. The reactor was operated at 203° C.-205° C. and 2.86-3.10 MPa with a feed of 30% glycerin in PG at a rate of 0.25 mL/min. A productivity of 0.12 g PG/(ml catalyst-hr) was achieved at 88% glycerin conversion and with 88% PG selectivity. The feed was switched to 12% PG, 26% glycerin and 62% dioxane and the flow rate doubled to 0.50 mL/min. Productivity increased to 0.24 g PG/(ml catalyst-hr) at a glycerin conversion of 85% and with a PG selectivity of 99%. The results of this experiment are summarized in Table 2, below, and show that the use of dioxane as the nonaqueous solvent in the present process resulted in substantially the same glycerin conversion, but with substantial increases in both productivity and PG selectivity.

TABLE 1

| | 60% glycerol/40% PG feed | | | | | | 37.5% glycerol/57.5% PG/5% H$_2$O feed | | | | | |
|---|---|---|---|---|---|---|---|---|---|---|---|---|
| | Hours | | | | | | | | | | | |
| | 755 | 820 | 827 | 843 | 851 | Av. | 867 | 875 | 891 | 899 | 915 | Av. |
| Temp (° C.) | 198 | 197 | 197 | 197 | 197 | | 197 | 196 | 197 | 197 | 198 | |
| Pressure(kPa) | 2.83 | 2.76 | 2.85 | 2.78 | 2.81 | | 2.83 | 2.78 | 2.69 | 2.79 | 2.73 | |
| H$_2$ flow (sccm) | 316 | 318 | 317 | 317 | 315 | | 317 | 316 | 318 | 334 | 315 | |
| Liquid flow (g/min) | 0.57 | 0.56 | 0.57 | 0.56 | 0.57 | | 0.64 | 0.64 | 0.64 | 0.63 | 0.63 | |
| Glycerol conversion | 86% | 80% | 78% | 79% | 77% | 80% | 67% | 67% | 67% | 68% | 67% | 67% |
| PG selectivity | 85% | 89% | 92% | 90% | 89% | 89% | 89% | 88% | 88% | 93% | 87% | 89% |

This example thus shows that the addition of 5% water resulted in a decrease in glycerin conversion to propylene glycol, although selectivity remained constant.

EXAMPLE 2

This example was conducted to illustrate the productivity, glycerin conversion and PG selectivity achieved when the hydrogenation process of the invention was conducted as a continuous process with dioxane as the nonaqueous solvent.

TABLE 2

| | 30% glycerol/60% PG feed | | | | | 26% glycerol/12% PG/62% dioxane feed | | | | |
|---|---|---|---|---|---|---|---|---|---|---|
| | Hours | | | | | | | | | |
| | 46.7 | 68.2 | 97.3 | 140.7 | 164.1 | 166.7[1] | 172.7[1] | 215.2 | 218.5 | 220.9 |
| Temp (° C.) | 202.7 | 202.9 | 202.9 | 202.9 | 202.9 | 204.7 | 204.8 | 205 | 204.9 | 205 |
| Pressure(kPa) | 2.83 | 2.88 | 2.85 | 2.90 | 2.91 | 2.81 | 2.84 | 3.01 | 2.80 | 2.89 |
| H$_2$ flow (sccm) | 53.8 | 53.7 | 53.7 | 53.7 | 53.8 | 53.6 | 53.7 | 53.6 | 53.7 | 53.7 |
| Liquid flow (g/min) | 0.290 | 0.267 | 0.238 | 0.265 | 0.250 | 0.518 | 0.541 | 0.519 | 0.533 | 0.530 |
| Productivity (g PG/g-hr) | 0.073 | 0.091 | 0.080 | 0.086 | 0.085 | 0.226 | 0.172 | 0.146 | 0.151 | 0.148 |
| Glycerin conversion | 75% | 89% | 88% | 88% | 88% | 85% | 85% | 76% | 75% | 76% |
| PG selectivity | 76% | 89% | 88% | 85% | 90% | 139% | 101% | 99% | 100% | 99% |

[1] These measurements were taken during the feed transition, the measurements at 215.2, 218.5 and 220.9 are representative of steady state conditions

EXAMPLE 3

This example was conducted to illustrate the glycerin conversion and PG selectivity achieved when the hydrogenation process of the invention was conducted as a batch process with various nonaqueous solvents.

A Johnson Matthey Pricat 60/35T copper chromium catalyst was activated by passing a 5% hydrogen/nitrogen gas stream at 100 cc/min over the pellets at 185° C. for about 16.7 hours, and then for 2 hours at 200° C. in a horizontal glass tube. The cooled, sealed glass tube containing the catalyst was transferred into a dry box and the catalyst transferred into a storage bottle.

The reactor utilized was a standard 300 mL stainless steel Parr high pressure reactor equipped with an air dispersion (hollow shaft) cruciform stirrer, a dip sampling tube, a catalyst basket and an internal thermocouple. The nonaqueous solvent was mixed with glycerin at a solvent/glycerin weight ratio of 70/30 and approximately 120 mL of this mixture added to the reactor. The reactor was loaded with 18 g of activated catalyst under inert atmosphere. The sealed reactor was removed to the laboratory and flushed (pressure/vent) four times with 50 psig nitrogen, then once with 400 psig hydrogen. The stirrer was started, the reactor was pressurized with hydrogen to 400 psig at room temperature and heated to 200° C. The pressure was maintained at 400-500 psig for the 10 hours run time.

Analysis of the resulting reaction product was conducted with a gas chromatograph (HP 6890) equipped with a flame ionization detector. Conversion was calculated as follows: Conversion=1−(moles glycerin charged/moles glycerin remaining). Selectivity was calculated as follows: (final moles PG−initial moles PG)/(initial moles glycerin−final moles glycerol). The results for each of the nonaqueous solvents tested are shown below in Table 3.

TABLE 3

| Nonaqueous Solvent | Productivity (g PG/(g catalyst/hr)) | Glycerine Conversion | PG Selectivity | Weight percent OH in solvent | Hydroxyl eq. wt. |
|---|---|---|---|---|---|
| Propylene glycol | 0.114 | 81 | 79 | 42 | 38 |
| Dipropylene Glycol | 0.129 | 82 | 87 | 25.3 | 67.1 |
| Dipropylene glycol methyl ether | 0.148 | 99 | 87 | 11.5 | 148 |
| Tripropylene glycol methyl ether with 11 weight percent PG | | 97 | 87 | 12.2 | 188 |
| Triethylene glycol | 0.055 | 40 | 70.6 | 22.6 | 75 |
| Triethylene glycol methyl ether | 0.103 | 65 | 80.7 | 10.4 | 164 |
| Polyethylene glycol (400 wt. av. mw) | 0.113 | 61.7* | 94 | 8.5 | 200 |
| Polyethylene glycol methyl ether (550 wt av mw) | 0.153 | 93 | 87 | 3.1 | 550 |

*Only 15.5 g activated catalyst were utilized in the example - extrapolating to 18 g, the conversion should be about 71.7%

This example thus shows that nonaqueous solvents with a lower weight percent OH in solvent, and thus a higher hydroxyl equivalent weight, can provide increased conversion and selectivity as compared to propylene glycol. This example also shows that ethers provided better conversion and selectivities than the corresponding glycols, i.e., triethylene glycol methyl ether provided better conversion and selectivity than triethylene glycol.

EXAMPLE 4

This example was conducted to illustrate the glycerin conversion and PG selectivity achieved when the hydrogenation process of the invention was conducted with a catalyst having little or no micropore volume and a surface area of greater than or equal to about 10 $m^2/g$.

A fixed bed reactor (½" diameter stainless steel tubular reactor) was loaded with 15 g of Raney® copper (W. R. Grace) 8-12 mesh, and having a total surface area of about 12 $m^2/g$. The area above and below the catalyst bed was filled with sand and the reactor was heated to 185° C. under a nitrogen flow to thoroughly dry the catalyst.

Figure 4:
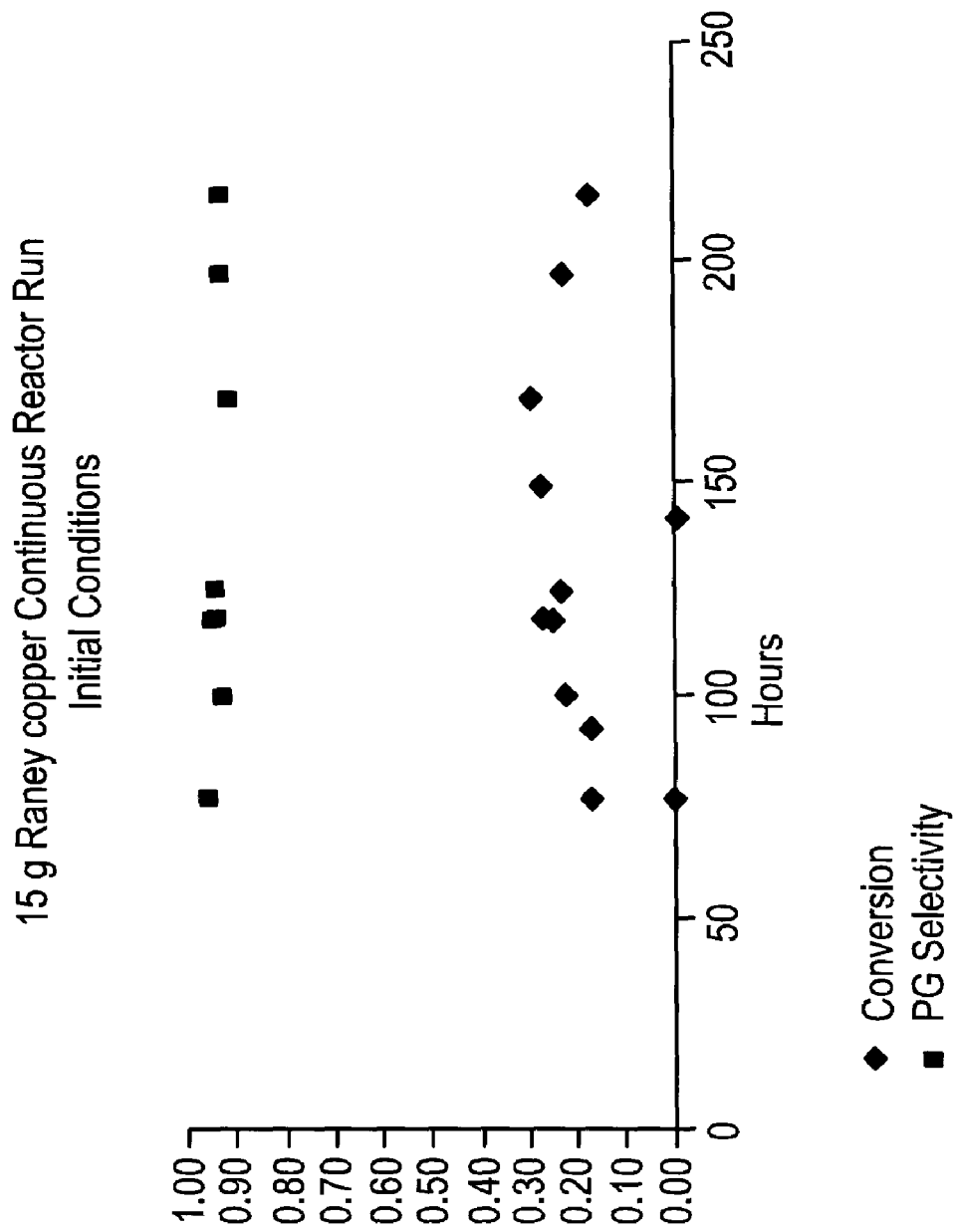
FIG. 4 is a graphical depiction of the glycerin conversion and propylene glycol selectivity for an improved hydrogenation process according to one embodiment of the invention performed as described in Example 4, over the first 200 hours of operation.

The reactor was fed 5% hydrogen in nitrogen at 255 sccm for 12 hours, at which time the feed was switched to 100% hydrogen at a flow rate of 79 sccm and the reactor pressurized to about 400 psi, or about 2.75 MPa. At 47 hours, a liquid feed comprising 30% glycerin in propylene glycol and at a flow of 0.35 ml/min was initiated. After 76 hours run time the temperature was raised to 190° C. and after 100 hours raised to 200° C. Glycerin conversion and PG selectivity for this flow rate are shown in FIG. 4. As shown, glycerin conversion is from about 18% to about 27%, with a PG selectivity of about 95%±1%.

At 214 hours, the liquid feed rate was reduced to 0.25 mL/min, and lowered again to 0.10 mL/min at 292 hours. At 331 hours, the $H_2$ flow was reduced to 26 sccm. Glycerin conversion and PG selectivity for these conditions is shown in FIG. 4. As shown, glycerin conversion is from about 50% to about 60% with a corresponding PG selectivity of about 96%±1%.

Figure 5:
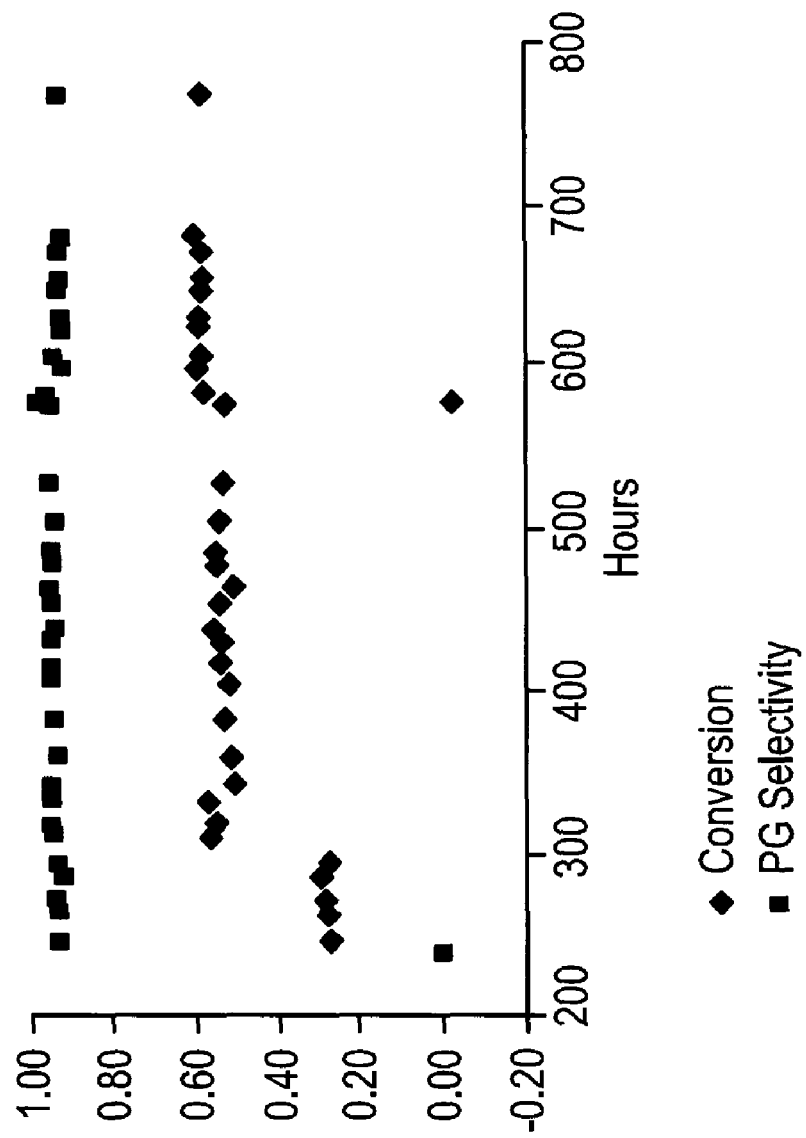
FIG. 5 is a graphical depiction of the glycerin conversion and propylene glycol selectivity for the improved hydrogenation process exemplified by Example 4, from 200 to 800 hours of operation.
Figure 6:
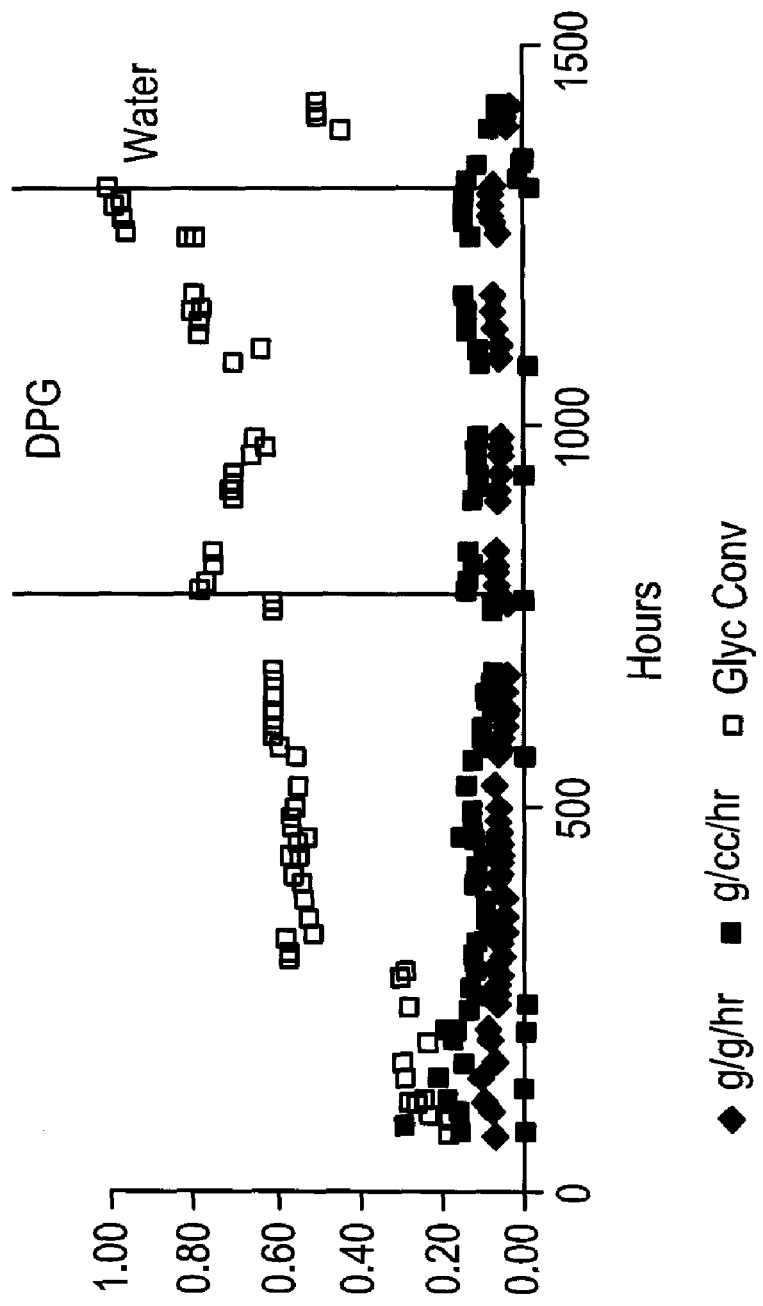
FIG. 6 is a graphical depiction of the glycerin conversion and propylene glycol selectivity for the improved hydrogenation process exemplified by Example 4, for the first 1500 hours of operation.
Figure 7:
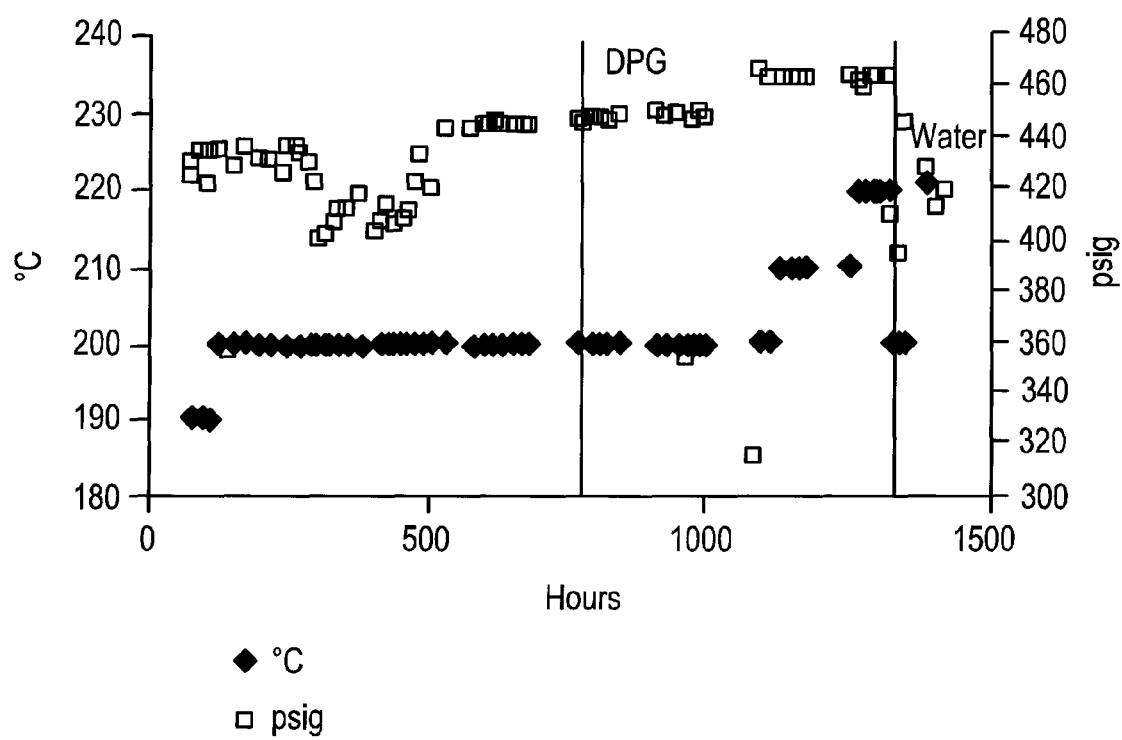
FIG. 7 is a graphical depiction of the temperatures and pressures for the improved hydrogenation process exemplified by Example 4, for the first 1500 hours of operation.

At 772 hours, the liquid feed was changed to 30% glycerin in dipropylene glycol. The data for the first 1500 hours of operation of this exemplary process is shown in FIGS. 5-7. As shown in FIG. 5, with propylene glycol as the solvent the glycerin conversion increased to about 60%. As shown in FIG. 6, when the solvent was switched from PG to DPG there was an initial increase in glycerin conversion to about 80%, however the glycerin conversion declined over time to about 65%. As shown in FIG. 7, the glycerin conversion was increased to about 80%, with no significant change in selectivity (96%) by raising the reaction temperature to 210° C. As also shown in FIG. 7, a further increase in glycerin conversion to about 95% was achieved by raising the reaction temperature further to 220° C. At 220° C. there was a decline in propylene glycol selectivity to about 93%. Finally, and as also shown in FIG. 7, switching the feed to 30% glycerin in water at 220° C. resulted in lower glycerin conversion (~50%) and lower propylene glycol selectivity (84%), once again illustrating the negative impact of water on propylene glycol productivity.

We claim:

1. A hydrogenation process comprising:
   (a) combining a reactant with a nonaqueous solvent to form a nonaqueous solvent/reactant mixture;
   (b) contacting the nonaqueous solvent/reactant mixture with hydrogen in the presence of a copper aluminum catalyst within an adiabatic reactor to form a reaction product; and
   (c) removing at least a portion of any water present in the reaction product with a water removal process driven at least in part by the heat of reaction of the hydrogenation reaction.

2. The process of claim 1, wherein the reactant is glycerin and the reaction product preferentially comprises propylene glycol.

3. The process of claim 1, wherein the nonaqueous solvent comprises a solvent with a hydroxyl wt % of less than about 45 and a hydroxyl weight equivalent of greater than about 30.

4. The process of claim 3, wherein the nonaqueous solvent comprises the reaction product and the glycerin is crude glycerin.

5. The process of claim 2, wherein the glycerin is crude glycerol.

6. A glycerin hydrogenation process comprising:
   (a) combining a glycerin feedstock with a nonaqueous solvent to provide a nonaqueous solvent/glycerin mixture having less than about 5 weight percent water; and
   (b) contacting the nonaqueous solvent/glycerin mixture with hydrogen in the presence of a catalyst within an adiabatic reactor to preferentially form a propylene glycol reaction product comprising less than about 17 wt % water.

7. The process of claim 6, wherein the propylene glycol reaction product comprises less than about 6 weight percent water.

8. The process of claim 6, wherein the nonaqueous solvent comprises a solvent with a hydroxyl wt % of less than about 45 and a hydroxyl weight equivalent of greater than about 30.

9. The process of claim 6, nonaqueous solvent comprises a reaction product, and prior to the contacting step, the reaction product/glycerin mixture is subjected to a distillation step.

10. The process of claim 9, wherein the product of the distillation step is subjected to a flash evaporator/condensing step prior to the contacting step.

* * * * *

UNITED STATES PATENT AND TRADEMARK OFFICE
CERTIFICATE OF CORRECTION

| | | |
|---|---|---|
| PATENT NO. | : 8,324,434 B2 | |
| APPLICATION NO. | : 12/918814 | |
| DATED | : December 4, 2012 | |
| INVENTOR(S) | : David C. Molzahn et al. | |

It is certified that error appears in the above-identified patent and that said Letters Patent is hereby corrected as shown below:

On the title page, item number (73), Assignee, "Dow Global Technologies, LLC" should read "Dow Global Technologies LLC"

Signed and Sealed this
Fourteenth Day of October, 2014

Michelle K. Lee
*Deputy Director of the United States Patent and Trademark Office*